United States Patent [19]

Thunberg

[11] Patent Number: 4,986,976
[45] Date of Patent: Jan. 22, 1991

[54] RECOVERY OF GLYCINE AND GLAUBER'S SALT FROM WASTE CRYSTAL LIQUORS

[75] Inventor: Jon C. Thunberg, Milford, N.H.

[73] Assignee: W. R. Grace & Co.-Conn., New York, N.Y.

[21] Appl. No.: 336,366

[22] Filed: Apr. 11, 1989

[51] Int. Cl.$^5$ .............. C01D 5/00; C01D 15/06; C07C 229/00
[52] U.S. Cl. ................... 423/551; 562/553; 562/554; 562/575
[58] Field of Search ............ 562/554, 553, 575; 423/184, 551

[56]  References Cited

U.S. PATENT DOCUMENTS

| | | | |
|---|---|---|---|
| 3,510,515 | 5/1970 | Colburn | 260/534 |
| 3,808,269 | 4/1974 | Bragdon et al. | 260/534 |
| 3,852,344 | 12/1974 | Bragdon et al. | 260/534 |
| 3,904,585 | 9/1975 | Thunberg et al. | 562/554 |
| 3,947,496 | 3/1976 | Thunberg et al. | 260/534 |
| 4,299,978 | 11/1981 | Nakayasu et al. | 562/554 |
| 4,691,054 | 9/1986 | Takafumi et al. | 562/554 |
| 4,818,409 | 4/1989 | Puetter et al. | 210/638 |

FOREIGN PATENT DOCUMENTS

| | | | |
|---|---|---|---|
| 53-13609 | 5/1978 | Japan | 562/575 |
| 1472840 | 9/1975 | United Kingdom . | |

Primary Examiner—Gregory A. Heller
Assistant Examiner—Timothy C. Vanoy
Attorney, Agent, or Firm—Kevin S. Lemack; William L. Baker

[57] ABSTRACT

Glycine and sodium sulfate decahydrate are separated from a starting aqueous solution containing glycine, sodium sulfate, and impurities, by forming a slurry which is a solid mixture of glycine and sodium sulfate decahydrate, followed by separation of the mixed crystals.

12 Claims, No Drawings

RECOVERY OF GLYCINE AND GLAUBER'S SALT FROM WASTE CRYSTAL LIQUORS

BACKGROUND OF THE INVENTION

1. Field of the Invention

This invention relates to the recovery of glycine and Glauber's Salt ($Na_2SO_4.10H_2O$) from solutions such as the liquor generated in the process of producing glycine.

2. Description of the Prior Art

Typical prior art processes for the recovery of glycine from sodium sulfate solutions are disclosed in U.S. Pat. Nos. 3,904,585 and 3,947,496.

U.S. Pat. No. 3,904,585, the disclosure of which is herein incorporated by reference, discloses a process of recovering glycine or B-alanine from a starting aqueous solution of sodium sulfate and the amino acid having a temperature above about 33° C., a pH of 4.5–8.5, a mole ratio of amino acid to sodium sulfate of about 1–5:1 and containing at least 5% amino acid. The process comprises forming a first slurry without precipitating the amino acid, (the first slurry being a mixture of precipitated sodium sulfate and first mother liquor), by evaporating water from the starting solution while maintaining its temperature within a range (from 60° or 70° C. up to the normal boiling point) effective for preventing the precipitation of the amino acid, separating the first mother liquor from the precipitated sodium sulfate, cooling the separated first mother liquor to a temperature within a range (33°–40° C.) effective for precipitating the amino acid, and separating and recovering the precipitated amino acid.

U.S. Pat. No. 3,947,496, the disclosure of which is herein incorporated by reference, discloses a process for recovering glycine from an aqueous starting solution of glycine and sodium sulfate that is similar to the process of the U.S. Pat. No. 3,904,585. The process comprises cooling the aqueous starting solution to a temperature above about 33° C. so that glycine is precipitated, and separating and recovering the precipitated glycine. Further steps include precipitating anhydrous sodium sulfate by evaporating water from the separated first mother liquor, etc.

The foregoing references use processes where the temperature is specified to be 33° C. or higher so as to avoid the precipitation of sodium sulfate decahydrate with the amino acid. These processes generate waste liquor streams which include a substantial amount of product. Impurities generated in the glycine production process, for example, are removed as a waste purge stream taken from the glycine mother liquor tank. The primary constituents of this stream are glycine, iminodiacetic acid (IDA) monosodium salt, $Na_2SO_4$, and water. A typical composition is about 18% glycine, 11% IDA expressed as $IDAH_2$, 12% $Na_2SO_4$, with the balance being water and unidentified organic compounds. Streams such as this have heretofore been discarded.

Other approaches to the recovery of amino acids include U.S. Pat. No. 3,510,575 where glycine is separated from $NH_4Cl$, U.S. Pat. No. 4,691,054 where amino acids are isolated by ion exchange from systems that are substantially free of inorganic ions (such as sodium sulfate), and U.S. Pat. No. 4,299,978 where the mother liquor after separation of glycine is acidified to isolate IDA bisulfate, and the new mother liquor formed is recycled to the process. Glauber's Salt is not generated.

SUMMARY OF THE INVENTION

The problems of the prior art have been overcome by 99e present invention which provides a process for separating glycine and sodium sulfate decahydrate (Glauber's Salt) from amino carboxylate containing solutions such as the waste liquors generated from the production of glycine.

It is therefore an object of the present invention to provide a process to minimize generation of waste from the production of glycine.

It is a further object of the present invention to provide a process for the recovery of value from the waste generated from the production of glycine.

It is a still further object of the present invention to provide a process which reduces disposal costs in the production of glycine.

According to the present invention, these and other objects which will become more apparent, are accomplished by providing a process for separating and recovering glycine and sodium sulfate decahydrate from a liquor containing glycine and sodium sulfate, which entails forming a slurry of precipitated glycine, sodium sulfate decahydrate and mother liquor, by, for example, adjusting the temperature of the liquor to a level sufficient to crystallize the glycine and Glauber's Salt, followed by separation of the mixed crystals from the mother liquor. The mixed crystals can be recycled to a point in the glycine production process.

DETAILED DESCRIPTION OF THE PREFERRED EMBODIMENT

The process of preparing glycine from the corresponding nitrile can be accomplished according to the following sequence of reactions:

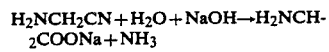

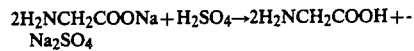

About 45% of the glycine now sent to waste in the glycine purge liquor from the foregoing process can be recovered, and at least a portion optionally recycled, in the process of the present invention. This can be accomplished by either batch or continuous cooling crystallization of the purge liquor to a temperature effective for precipitating the glycine and Glauber's Salt. In the batch process, solutions containing glycine, sodium sulfate, and impurities, such as waste liquor and recycled liquor produced in the process for the production of glycine, are charged to a cooling crystallizer. The mixture is cooled to a temperature effective for precipitating the glycine and Glauber's Salt. Glauber's Salt seed crystals can be added at about the saturation temperature of sodium sulfate decahydrate in the solution. Similarly, glycine seed crystals can be added to the solution. The recovered solid, which is a mixed wet cake comprising glycine and Glauber's Salt, is separated from the mother liquor by, for example, centrifugation. The solid can be recycled to an earlier point in the production process. For example, in the production process disclosed in U.S. Pat. No. 3,904,585, the solid can be recycled to the first slurry formation step. At least a portion of the mother liquor (e.g., 50%) can be recycled to the purge crystallizer to reduce the slurry density.

In another embodiment, a continuous crystallization can be used. A slurry of glycine, Glauber's Salt and liquor is prepared at the operating temperature (e.g., about 5° C.) by any suitable means. The primary consideration is to generate an initial slurry before continuous operation can start. One method for start-up is to charge the crystallizer with warm liquor (e.g., 40° C.) and slowly reduce the temperature, as in the batch mode. Glycine seed can be added in the beginning, and Glauber's Salt seed at about 18° C. As the slurry thickens upon further cooling, separation is begun (e.g., by centrifugation), with a portion of the liquor (e.g., 50%), being recycled to the crystallizer to maintain a manageable slurry density. Once the system is equilibrated at the operating temperature (e.g., 5° C.), continuous addition of fresh waste liquor is fed into the slurry (for example, directly into the crystallizer or into the stream feeding the crystallizer) while cooling to maintain the operating temperature. Both the glycine and Glauber's Salt crystallize, since the crystallizer operates at a temperature below the saturation temperature of both. Slurry is constantly withdrawn and subjected to separation. A portion of the liquor can be continuously recycled to the crystallizer to reduce the slurry density.

It is important that the entrainment of liquor in the wet cake be kept to a minimum, since this liquor is rich in impurities which should not be recycled to the glycine or $Na_2SO_4$ crystallizers in the glycine production process. The glycine:IDA weight ratio of the cake is a measure of the entrained liquor. Although a weight ratio of about 5:1 is operable, a ratio of at least about 10:1 is preferred to avoid recycle of excessive amounts of impurities, and is similar to that ratio in the incoming sodium glycinate. Any ratio greater than 10:1 can be used.

Separation is preferably accomplished by centrifugation, although other forms of separation such as filtration or decantation could be used. Suitable centrifuges include the traditional vertical perforated bowl centrifuge, which provides excellent separation of entrained liquor. A speed setting corresponding to a centrifugal force of about 500 g can be used. A setting corresponding to a centrifugal force of more than about 1000 g is preferred, with a force of about 2000 g being most preferable.

In the glycine production process, wash water can be used to wash the cake generated in the glycine production step free of sodium sulfate. However, this wash causes about 25-30% of the glycine in the cake to redissolve, which increases the glycine:IDA ratio in the mother liquor purge stream that can be the feedstock for the instant process. By excluding the wash water, the glycine:IDA ratio in the purge stream is minimized, thereby increasing the recovery of glycine by about 2% in the instant process. If such a concentrated purge is used, it can be diluted with water to adjust the total solids level to a range of about 40-60%. A total solids level of about 48-54% is preferred, with a level of about 52% being especially preferred.

The temperature at which glycine and Glauber's Salt are precipitated is a function of the concentration of glycine and the sodium sulfate in the solution. The typical waste purge stream from the process for the production of glycine has a composition of about 18% glycine and about 12% sodium sulfate. The preferred temperature to which such a solution should be cooled is about 5° C. Those skilled in the art will be able to determine the necessary temperature to which the particular stream must be cooled to precipitate glycine and Glauber's Salt.

A glycine stream having the aforementioned composition precipitates because of the decreased solubility at about 5° C. as compared to its solubility in the starting solution, which has a temperature of about 40° C. Simultaneously, solute (i.e., water) is removed with the $Na_2SO_4$ which crystallizes $Na_2SO_4.10H_2O$. Because this water becomes part of the solids in the slurry, the slurry density becomes high. In the continuous system, the slurry density can be adjusted appropriately by continuously recycling saturated 5° C. mother liquor back to the crystallizer.

The recovered solid, which is a mixture of glycine, Glauber's Salt, plus some entrained liquor, can be recycled to the mix tank that contains the feed to the $Na_2SO_4$ crystallizer in the glycine production process. Water is added to the solid to create a pumpable stream. From that crystallization, the $Na_2SO_4$ is isolated as anhydrous $Na_2SO_4$. The mother liquor remaining after separation of the $Na_2SO_4$ contains the glycine which is then crystallized in the succeeding glycine crystallizer. A portion of the mother liquor remaining after separation of glycine is the purge liquor feed stock (with or without wash) for the present process.

The instant invention will be better understood by referring to the following specific but non-limiting examples. It is understood that said invention is not limited by these procedures which are offered merely as illustrations; it is also understood that modifications can be made without departing from the spirit and scope of the invention.

EXAMPLE 1

The typical purge liquor generated in the glycine production process has a starting temperature of about 40° C. A study of the cooling rate was conducted in a batch cooling crystallizer where 1200 grams of purge (composition: 18.8% glycine, 11.4% $IDAH_2$, 10.6% $Na_2SO_4$) was equilibriated at 40° C., seeded with 25 grams of mixed seed, and linearly program-cooled to 5° C. at rates of 2.19° C./hr, 5.83° C./hr, and 17.5° C./hr. Experiments cooling slurries to 10° C. and 15° C. also were run. Slurries cooled to 5° C. using cooling rates of either 2.19° C./hr or 5.83° C./hr produced clean cakes which were indistinguishable. The slurry cooled at the rate of 17.5° C./hr produced a sticky wet cake. The analysis of the slurries cooled at 2.19° C./hr and 5.83° C./hr is shown below:

|  | Air Dried Solid From Cooling Rates of: | |
| --- | --- | --- |
|  | 2.19° C./hr (16 Hr) | 5.83° C./hr (6 hr) |
| Recovery of Glycine from the Feed | 61% | 60% |
| % Glycine | 54.7 | 54.1% |
| % IDA $H_2$ | 6.6% | 7.5% |
| Glycine: $IDAH_2$ Ratio | 8.28:1 | 7:21:1 |

The saturation temperature of Glauber's Salt in the glycine purge slurry was determined to be about 18°-20° C. Material crystalized by adding $Na_2SO_4.10H_2O$ seed at about the saturation temperature produced uniform, easily centrifuged slurries without thixotropic properties.

EXAMPLE 2

Glycine can be isolated as the acid salt Triglycine Sulfate (Glycine)$_3$.H$_2$SOhd 4, at low pH. A glycine-containing purge containing 18.8% glycine, 11.4% IDAH$_2$, and 10.6% Na$_2$SO$_4$ was acidified with 25.6 g of 93% H$_2$SO$_4$ to lower the pH to 3.0, and with 226 g of 93% H$_2$SO$_4$ to lower the pH to 2.0, seeded with (gly)$_3$.H$_2$SO$_4$ and cooled to 5° C. over 6 hr. The pH 2.0 slurry had to be centrifuged at approximately 23° C. as well as 5° C. to maintain a workable slurry density. Table I shows the results:

TABLE I

|  | Air Dried Solid From | |
|---|---|---|
|  | pH 3.0 | pH 2.0 |
| % of Glycine Recovered | 35% | 64% |
| % Glycine | 27.8% | 32.5% |
| % IDA H$_2$ | 3.0% | 15.7% |

The solid was heavily contaminated with IDA and required a large consumption of H$_2$SO$_4$. Accordingly, lowering of the pH is not practical unless such considerations are not deleterious to the intended application.

EXAMPLE 3

Batch Crystallization of Glycine Purge Liquor 1250 g of glycine purge containing 19.8% glycine and 12.9% Na$_2$SO$_4$, was diluted with 60 g of water to reduce the total solids content to 52.0%. This solution was charged to a 1 liter batch cooling crystallizer. The temperature was equilibrated at 40° C. and then seeded with 10 g of glycine. The mixture was linearly cooled to 5° C. over 4 hr. The slurry was seeded with 5 g of Glauber's Salt at 18° C. to initiate crystallization of this salt. The solid was recovered with a centrifuge operating at about 550 g. 311 g of air-dried solid was recovered which contained 37.7% glycine and 49.4% Na$_2$SO$_4$, which represented recoveries of 50% and 82%, respectively.

EXAMPLE 4

Continuous Crystallization of Glycine Purge Liquor

A 1 liter batch crystallization was run as described in Example 3 and mixed with an approximately equal amount of liquor generated from previous experiments. This mixture, chilled to 5° C., was charged to a 2 liter crystallizer. Fresh 40° C. glycine purge liquor was continually pumped into the crystalizer at a rate of about 24 g/min; this gave an average residence time in the crystallizer of 2 hr. The crystallizer was continually cooled to maintain the slurry at 5° C.

When the slurry level reached maximum, about 25% of the slurry was pumped directly into a centrifuge. The centrate was collected in a tared beaker, weighed, and then 50% of the collected centrate was added back to the crystallizer. The pre-tared centrifuge basket was weighed and the collected solids were scraped into a dish and air dried. The solids were later dried under vacuum at 60° C.

This process was continued without interruption for 24 hr, or a total of about 12 residence times. Over the course of this experiment, 34.3 kg of purge liquor was charged and 12.9 kg of wet solid was recovered. The average composition of the wet solids was 42.6% glycine and 44.1% Na$_2$SO$_4$, representing recoveries of 49% and 78%, respectively.

What is claimed:

1. In a process for recovering glycine from a starting aqueous solution consisting essentially of sodium sulfate, glycine, and water, wherein said process comprises:
   a. forming a first slurry having a temperature effective for preventing precipitation of glycine, the first slurry being a mixture of precipitated sodium sulfate and a first mother liquor, the first mother liquor being a second aqueous solution consisting essentially of sodium sulfate, glycine, and water, by evaporating water from the starting aqueous solution while maintaining its temperature within a range effective for preventing the precipitation of glycine;
   b. separating the first mother liquor from the precipitated sodium sulfate;
   c. cooling the separated first mother liquor to a temperature within a range effective for precipitating glycine to form a second slurry, the second slurry being a mixture of precipitated glycine and a second mother liquor, the second mother liquor being a third aqueous solution consisting essentially of sodium sulfate, glycine, and water; and
   d. separating and recovering the precipitated glycine, the improvement comprising:
   e. cooling said second mother liquor to a temperature within a range effective for precipitating a mixture of glycine and sodium sulfate decahydrate to form a third slurry, the third slurry comprising a mixture of precipitated glycine and sodium sulfate decahydrate and a third mother liquor; and
   f. separating the precipitated glycine and sodium sulfate decahydrate from the third mother liquor.

2. The process of claim 1 comprising the further step of recycling at least a portion of said precipitated glycine and sodium sulfate decahydrate to step a.

3. The process of claim 1 comprising the further step of recycling at least a portion of said third mother liquor to step e.

4. The process of claim 1 further comprising adding glycine seed crystals to the second mother liquor prior to cooling said second mother liquor.

5. The process of claim 1 further comprising adding sodium sulfate decahydrate seed crystals during the cooling of said second mother liquor.

6. The process of claim 5 wherein the sodium sulfate decahydrate seed crystals are added at about the saturation temperature of sodium sulfate decahydrate in said second mother liquor.

7. In a process for recovering glycine from a starting aqueous solution consisting essentially of sodium sulfate, glycine, and water, wherein said process comprises:
   a. forming a first slurry having a temperature effective for preventing precipitation of glycine, the first slurry being a mixture of precipitated sodium sulfate and a first mother liquor, the first mother liquor being a second aqueous solution consisting essentially of sodium sulfate, glycine, and water, by evaporating water from the starting aqueous solution while maintaining its temperature within a range effective for preventing the precipitation of glycine;
   b. separating the first mother liquor from the precipitated sodium sulfate;
   c. cooling the separated first mother liquor to a temperature within a range effective for precipitating glycine to form a second slurry, the second slurry being a mixture of precipitated glycine and a second mother liquor, the second mother liquor being a third aqueous solution consisting essentially of sodium sulfate, glycine, and water; and d. separating and recovering the precipitated glycine, the improvement comprising:

e. preparing a third slurry of glycine, sodium sulfate decahydrate and a third mother liquor at about the temperature specified in step g;

f. feeding said third slurry into a continuous crystallizer;

g. continuously feeding said second mother liquor into said third slurry while cooling to maintain the temperature in a range effective for precipitating glycine and sodium sulfate decahydrate to form fourth slurry, said fourth slurry comprising a mixture of precipitated glycine and sodium sulfate decahydrate and a fourth mother liquor; and h. continuously separating the precipitated mixture of glycine and sodium sulfate decahydrate from the fourth mother liquor.

8. The process of claim 7 comprising the further step of recycling at least a portion of said separated glycine and sodium sulfate decahydrate to step a.

9. The process of claim 7 comprising the further step of continuously recycling at least a portion of said fourth mother liquor to step g.

10. The process of claim 7 further comprising adding glycine seed crystals to the second mother liquor prior to cooling said second mother liquor.

11. The process of claim 7 further comprising adding sodium sulfate decahydrate seed crystals during the cooling of said second mother liquor.

12. The process of claim 11 wherein the sodium sulfate decahydrate seed crystals are added at about the saturation temperature of sodium sulfate decahydrate in said second mother liquor.

* * * * *